(12) United States Patent
Vrabec et al.

(10) Patent No.: US 11,865,342 B2
(45) Date of Patent: Jan. 9, 2024

(54) SLURRY ELECTRODES FOR DIRECT CURRENT NERVE CONDUCTION BLOCK

(71) Applicant: Case Western Reserve University, Cleveland, OH (US)

(72) Inventors: Tina L. Vrabec, Cleveland, OH (US); Jesse S. Wainright, Cleveland, OH (US); Niloy Bhadra, Cleveland, OH (US); Kevin L. Kilgore, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 4 days.

(21) Appl. No.: 17/890,327

(22) Filed: Aug. 18, 2022

(65) Prior Publication Data
US 2022/0401733 A1 Dec. 22, 2022

Related U.S. Application Data

(63) Continuation of application No. 16/957,808, filed as application No. PCT/US2018/067811 on Dec. 28, 2018, now Pat. No. 11,426,585.
(Continued)

(51) Int. Cl.
*A61N 1/04* (2006.01)
*A61N 1/05* (2006.01)
(Continued)

(52) U.S. Cl.
CPC ......... *A61N 1/36071* (2013.01); *A61N 1/048* (2013.01); *A61N 1/0456* (2013.01); *A61N 1/0556* (2013.01); *A61N 1/20* (2013.01)

(58) Field of Classification Search
CPC .. A61N 1/36071; A61N 1/0456; A61N 1/048; A61N 1/0556; A61N 1/20;
(Continued)

(56) References Cited

U.S. PATENT DOCUMENTS

| 2010/0016929 A1* | 1/2010 | Prochazka ........... A61B 5/0028 607/72 |
| 2011/0160798 A1* | 6/2011 | Ackermann, Jr. .... A61L 31/048 607/46 |
| 2017/0005504 A1 | 1/2017 | Rho et al. |

FOREIGN PATENT DOCUMENTS

| WO | 2013/188753 A1 | 12/2013 |
| WO | 2017/062272 A1 | 4/2017 |
| WO | 2018/217999 A1 | 11/2018 |

OTHER PUBLICATIONS

Amatya, Bhasker, et al. "Non pharmacological interventions for spasticity in multiple sclerosis." Cochrane database of systematic reviews 2 (2013).
(Continued)

*Primary Examiner* — Carl H Layno
*Assistant Examiner* — Anh-Khoa N Dinh
(74) *Attorney, Agent, or Firm* — TAROLLI, SUNDHEIM, COVELL & TUMMINO, LLP

(57) ABSTRACT

Slurry electrodes can deliver direct current (DC) nerve conduction block to neural tissue. Such slurry electrodes can include an ionically conductive membrane having a first side and a second side. Slurry electrodes can also include a mechanism that is configured to encapsulate a slurry against the first side of the ionically conductive membrane. The slurry can include an ionically conductive material and a plurality of electrically conducting high surface area particles. The mechanism and the first side of the ionically conductive membrane make up a housing for the slurry. Slurry electrodes can also include a connector configured to establish an electrical connection between the slurry and the DC generator.

20 Claims, 4 Drawing Sheets

Related U.S. Application Data

(60) Provisional application No. 62/611,091, filed on Dec. 28, 2017, provisional application No. 62/611,075, filed on Dec. 28, 2017, provisional application No. 62/611,086, filed on Dec. 28, 2017.

(51) Int. Cl.
  *A61N 1/36* (2006.01)
  *A61N 1/20* (2006.01)

(58) Field of Classification Search
  CPC ........ A61N 1/0551; H01G 4/35; H01G 2/103; H01G 4/005; H01G 4/12; H01G 4/40; A61M 2025/0046; A61M 25/0068; A61F 5/4553; A61F 5/4556; A61F 2/02; A61F 2210/0085; A61F 2230/0069; A61F 2240/004; A61F 2250/0059
  See application file for complete search history.

(56) References Cited

OTHER PUBLICATIONS

Baron, Ralf. "Neuropathic pain: a clinical perspective." Sensory Nerves. Springer, Berlin, Heidelberg, 2009. 3-30.

Bhadra, Niloy, et al. "Reversible conduction block in peripheral nerve using electrical waveforms." Bioelectronics in medicine 1.1 (2018): 39-54.

Canadian Office Action for corresponding Canadian Application Serial No. 3,086,910, dated Jul. 29, 2021, pp. 1-4.

Franke, M., et al. "Chronic bladder control post SCI via electric KHFAC pudendal nerve block." Proc. IEEE EMBS Conf. Neural Eng.. 2013.

Koch, Horst, et al. "Treatment of painful neuroma by resection and nerve stump transplantation into a vein." Annals of plastic surgery 51.1 (2003): 45-50.

Lin, Yin-Tsong, et al. "Dual-channel neuromodulation of pudendal nerve with closed-loop control strategy to improve bladder functions." J Med Biol Eng 34.34 (2014): 82-9.

Lundstrom, Erik, et al. "Four-fold increase in direct costs of stroke survivors with spasticity compared with stroke survivors without spasticity: the first year after the event." Stroke 41.2 (2010): 319-324.

Naples, Gregory G., et al. "A spiral nerve cuff electrode for peripheral nerve stimulation." IEEE transactions on biomedical engineering 35.11 (1988): 905-916.

PCT International Search Report and Written Opinion for the corresponding International Application Serial No. PCT/US2018/067811, dated Mar. 18, 2019, pp. 1-13.

Rizzo, M. A., et al. "Prevalence and treatment of spasticity reported by multiple sclerosis patients." Multiple Sclerosis Journal 10.5 (2004): 589-595.

Stokvis, Annemieke, J. Henk Coert, and Johan W. van Neck. "Insufficient pain relief after surgical neuroma treatment: Prognostic factors and central sensitisation." Journal of plastic, reconstructive & aesthetic surgery 63.9 (2010): 1538-1543.

Tiede, Jeffrey, et al. "Novel spinal cord stimulation parameters in patients with predominant back pain." Neuromodulation: Technology at the Neural Interface 16.4 (2013): 370-375.

\* cited by examiner

SLURRY ELECTRODES FOR DIRECT CURRENT NERVE CONDUCTION BLOCK

RELATED APPLICATIONS

The present application is a continuation application of U.S. patent application Ser. No. 16/957,808, filed Jun. 25, 2020, now U.S. Pat. No. 11,426,585 B2, which is a U.S. National Stage application of PCT/US2018/067811, filed Dec. 28, 2018, which claims priority to U.S. Provisional Application Ser. No. 62/611,075, filed Dec. 28, 2017, U.S. Provisional Application Ser. No. 62/611,086, filed Dec. 28, 2017, and U.S. Provisional Application Ser. No. 62/611,091, filed Dec. 28, 2017, the entireties of which are hereby incorporated herein by reference.

TECHNICAL FIELD

The present disclosure relates generally to direct current (DC) nerve conduction block and, more specifically, to slurry electrodes that can deliver the DC nerve conduction block to neural tissue.

BACKGROUND

Many neurological diseases are characterized by unwanted neural activity conducted within neural tissue (e.g., along peripheral axons) and inducing pathological effects (e.g., within an end organ). The application of an electrical field to neural tissue has been shown to produce an electrical block of such conduction of neural activity within the neural tissue. Kilohertz frequency alternating current (KHFAC), for example, can produce a steady state depolarization in the neural tissue, leading to KHFAC nerve conduction block. Although KHFAC nerve conduction block has been widely explored and appeared promising, it has not been adopted clinically due to the production of an undesirable onset response in the nerve. While it is possible to completely neutralize the onset response by applying a brief direct current (DC) waveform through a flanking electrode, nerve conduction is lost after several applications of the DC waveform.

DC nerve conduction block has become an attractive candidate for achieving block without the onset response. Indeed, application of a DC alone can provide either depolarization or hyperpolarization (depending on the polarity of the signal) and produce a complete conduction block without the onset response of the KHFAC nerve conduction block. Additionally, anodic break excitation at cessation can be prevented by the design of the DC nerve conduction block waveform. However, the likelihood of the DC nerve conduction block causing damage to the nerve (e.g., due the production of non-reversible Faradaic reaction products during stimulation) has kept the DC nerve conduction block from being adopted clinically.

SUMMARY

The present disclosure relates generally to direct current (DC) nerve conduction block and, more specifically, to slurry electrodes that can deliver the DC nerve conduction block to neural tissue. Such slurry electrodes can apply the DC nerve conduction block safely, avoiding the generation of the damaging non-reversible reaction products in the interface with the neural tissue.

In one aspect, the present disclosure can include a device (also referred to as a slurry electrode) that can be used to deliver DC to neural tissue to block conduction in the neural tissue when coupled to a DC generator. The device can include an ionically conductive membrane having a first side and a second side. The device can also include a mechanism that is configured to encapsulate a slurry against the first side of the ionically conductive membrane. The slurry can include an ionically conductive material and a plurality of electrically conducting high surface area particles. The mechanism and the first side of the ionically conductive membrane make up a housing for the slurry. The device can also include a connector configured to establish an electrical connection between the slurry and the DC generator.

In another aspect, the present disclosure can include a system that can block conduction in neural tissue. The system can include a DC generator that generates a DC. The DC generator can be coupled to at least one device (also referred to as a slurry electrode) that can deliver the DC to block conduction in the neural tissue. The at least one device can include an ionically conductive membrane having a first side and a second side and a mechanism that is configured to encapsulate a slurry against the first side of the ionically conductive membrane. The slurry can include an ionically conductive material and a plurality of electrically conducting high surface area particles. The mechanism and the first side of the ionically conductive membrane make up a housing for the slurry. The system can also include a connector configured to establish an electrical connection between the slurry of the at least one device and the DC generator.

In a further aspect, the present disclosure can include a method for establishing DC nerve conduction block in neural tissue. A device (also referred to as a slurry electrode), coupled to a DC generator, can be placed in proximity to neural tissue. The device can include an ionically conductive membrane having a first side and a second side and a mechanism that is configured to encapsulate a slurry against the first side of the ionically conductive membrane. The slurry can include an ionically conductive material and a plurality of electrically conducting high surface area particles. The mechanism and the first side of the ionically conductive membrane make up a housing for the slurry. The coupling can be established by a connector creating a connection between a slurry within the device and the DC generator. A DC, generated by the DC generator, can be applied to the nerve by the device. The DC can have an amplitude sufficient to alter transmission of action potentials in the neural tissue. The DC is converted to an ionic current within the slurry electrode, and the ionic current establishes a nerve conduction block in the neural tissue, altering the transmission of the action potentials in the neural tissue.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
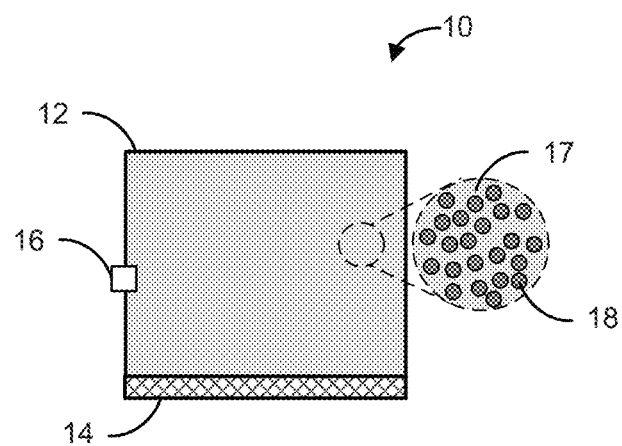
FIG. 1 is a schematic diagram showing an example of a slurry electrode that can be used to deliver direct current (DC) to a neural tissue to block conduction in the neural tissue in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "nerve conduction block" can refer to the attenuation of conduction in neural tissue due to a change in the electric field caused by application of an electrical signal to the nerve. Attenuating conduction can refer to extinguishing 100% or less (e.g., 90%, 80%, 70%, 60%, 50%, or the like) of the action potentials traveling through the target neural tissue. In one example, when nerve conduction is attenuated, a target nerve will have an increased activation threshold and thereby make the target nerve more difficult to excite. In another example, the conduction velocity within the target nerve can be decreased when nerve conduction is attenuated.

As used herein, the term "direct current nerve conduction block" or "DC nerve conduction block" can refer to the application of a direct current to a nerve to alter conduction in the nerve. As used herein, a DC nerve conduction block can be considered "safe" when the block occurs without producing non-reversible Faradaic reaction products in an interface between neural tissue and the device delivering the DC nerve conduction block to the neural tissue (e.g., an electrode).

As used herein, the terms "direct current" or "DC" can refer to a unidirectional flow or movement of electric charge carriers. A DC can be cathodic or anodic. In some instances, the DC can be applied as the first phase of a biphasic waveform. The second phase of the biphasic waveform can either reverse 100% of the total charge delivered by the first phase (as a charge-balanced biphasic waveform) or reverse less than 100% of the total charge delivered by the first phase (as a charge imbalanced biphasic waveform).

As used herein, the term "nerve" can refer to one or more fibers that employ electrical and chemical signals to transmit motor, sensory, and/or autonomic information from one body part to another. A nerve can refer to either a component of the central nervous system or the peripheral nervous system.

As used herein, the term "neurological disorder" can refer to a condition or disease characterized at least in part by abnormal conduction in one or more nerves. In some instances, a subject suffering from a neurological disorder can experience pain and/or muscle spasticity. Examples of neurological disorders can include stroke, brain injury, spinal cord injury (SCI), cerebral palsy (CP), multiple sclerosis (MS), etc.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "medical professional" can refer to an individual who provides care to a patient. A medical professional can be, for example, a doctor, a physician's assistant, a student, a nurse, a caregiver, or the like.

II. Overview

The present disclosure relates generally to direct current (DC) nerve conduction block. DC nerve conduction block is attractive for many applications because it is fast acting, reversible, onset free, and easy to modulate. However, DC nerve conduction block has not been used clinically due to its high likelihood of causing nerve damage. When DC is applied to neural tissue via traditional electrodes (e.g., through traditional surface electrodes, percutaneous electrodes, subcutaneous electrodes, or the like) for a prolonged period of time, Faradaic reactions like hydrogen evolution, oxygen evolution, chlorine evolution, or the like, can occur and cause damage to the interface between the neural tissue and a device (e.g., electrode) applying the DC. Hydrogen and oxygen evolution can cause potentially damaging changes in pH, while chlorine evolution generates a corrosive, toxic gas.

The present disclosure relates, more specifically, to slurry electrodes that can deliver the DC nerve conduction block to neural tissue without generating damaging Faradaic reaction products at the electrode-tissue interface. The slurry electrodes includes a slurry of an ionically conducting material combined with electrically conducting high surface area particles, which can be encapsulated in contact with an ionically conductive membrane to provide a high capacitance electrode with a small form factor. The slurry facilitates charge transfer from the electrically conducting high surface area particles to the ionically conducting material. The ionically conductive membrane prevents the possibility of migration of the slurry material, while allowing ionic current to flow through and deliver the DC nerve conduction block. The slurry electrodes described herein enable the use of DC nerve conduction block in a variety of clinical and experimental applications.

III. Slurry Electrodes

Figure 3:
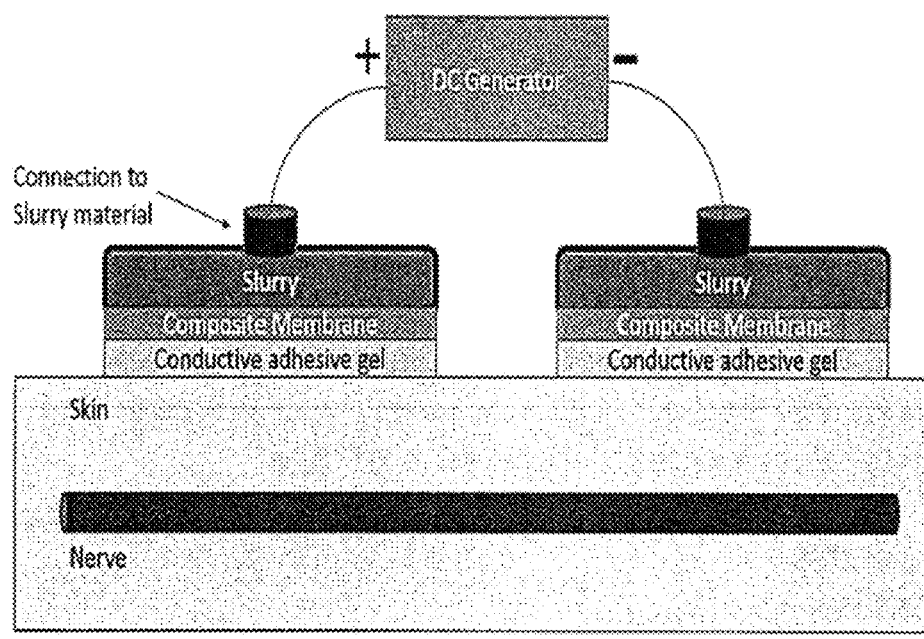
FIGS. 3-4 show examples of a slurry electrode in FIG. 1 being used for surface/transcutaneous application of DC.
Figure 6:
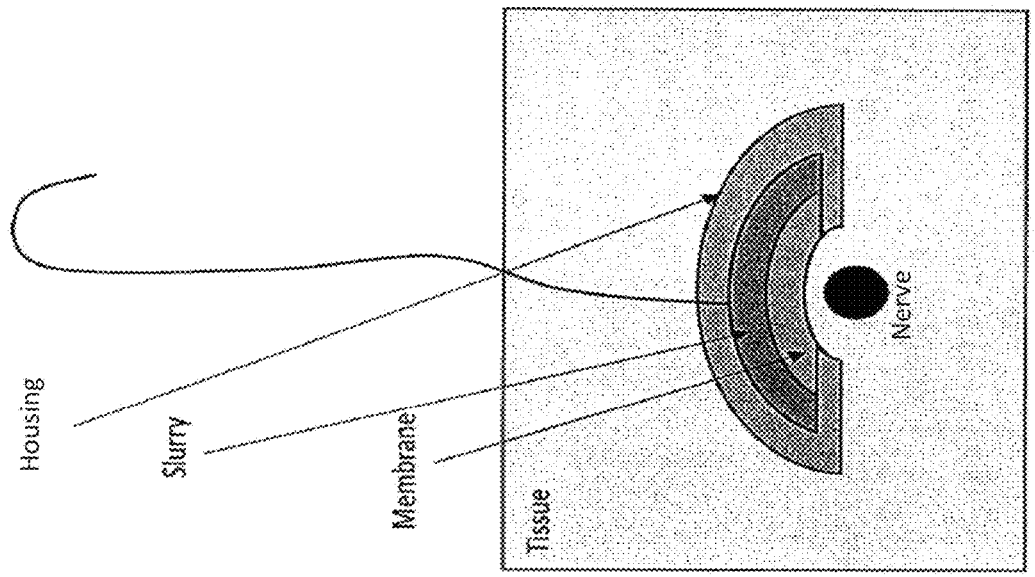
FIG. 6 shows an example of a slurry electrode in FIG. 1 being used for subcutaneous application of DC.
Figure 5:
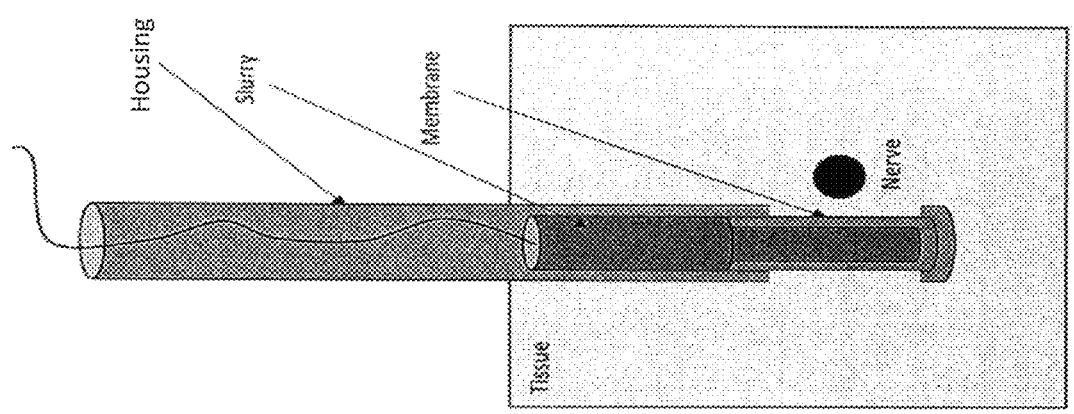
FIG. 5 shows an example of a slurry electrode in FIG. 1 being used for percutaneous application of DC.

One aspect of the present disclosure can include a slurry electrode 10 (FIG. 1) that can be used to deliver direct current (DC) nerve conduction block to neural tissue. As an example, the slurry electrode can be configured for surface/transcutaneous application of the DC nerve conduction block (as a disposable electrode, shown in FIGS. 3—side-by-side on the skin surface—and 4—placed on opposite sides of the nerve on the skin surface). In another example, the slurry electrode can be configured for percutaneous application of the DC nerve conduction block (FIG. 5). As a further example, the slurry electrode can be configured for subcutaneous application of the DC nerve conduction block, such as a cuff that at least partially encircles a nerve (FIG. 6). In any of these examples, damaging Faradaic reaction products can be kept away from the neural tissue, happening in the slurry alone. Notably, the slurry electrode 10, in any form, can enable the use of DC nerve conduction block in a variety of clinical and experimental applications (see VI. Examples for a description of certain example clinical applications).

As illustrated, the slurry electrode 10 includes a housing mechanism 12, an ionically conductive membrane 14, and a connector 16. The slurry is encapsulated by the housing mechanism 12, which creates a housing for the slurry with the ionically conductive membrane 14. The housing mechanism 12 can be, for example, biocompatible tubing, a surface electrode housing, a cuff electrode material, or the like. The slurry electrode 10 can have a high capacitance that is configurable for the application. In some instances, the size of the housing mechanism 12 can relate to the capacitance, so a larger housing mechanism 12 can have a larger capacitance. For example, when used as a percutaneous or subcutaneous electrode, an entire volume of the housing mechanism 12 can be filled with slurry, creating a large volume of slurry and increasing the capacitance of the slurry electrode.

At least a portion of the housing mechanism 12 covered by the ionically conductive membrane 14 can allow the slurry to interface with the ionically conductive membrane 14. The slurry can be in contact with the ionically conductive membrane 14 to provide a high capacitance electrode. The ionically conductive membrane 14 prevents the possibility of migration of the slurry material, while allowing ionic current to flow through and deliver the DC nerve conduction block as an ionic current. As an example, the ionically conductive membrane 14 can include a non-porous film (referred to as a second side that does not contact the slurry and is designed to prohibit the slurry from escaping the housing) disposed on a porous substrate material (referred to as a first side that contacts the slurry). The ionically conductive membrane 14 is described in detail in application PCT/US2017/019644, the subject matter of which is incorporated herein by reference in its entirety.

The connector 16 can be used to establish an electrical connection between the slurry and a DC generator. The connector 16 can contact a portion of the slurry, but does not contact the ionically conductive membrane 14. Examples of the connector 16 can include a wire, a foil, a mesh, and/or at least a portion of the housing mechanism 12.

The slurry includes a plurality of electrically conducting high surface area particles 18 dispersed within an ionically conducting material 17. The slurry allows for non-Faradaic charge transfer from the electrically conducting high surface area particles to the ionically conducting material. The electrically conducting high surface area particles 18 can conduct an electric current. The ionically conducting material 17 can conduct an ionic current. The electrical current from the electrically conducting high surface area particles 18 can be converted to the ionic current transmitted by the ionically conducting material 17, which can be delivered through the ionically conductive membrane 14 to the neural tissue.

The ionically conducting material 17 can be a solution or a gel that includes an ionically-conductive material, such as a salt. The salt can be any salt, such as potassium chloride, sodium lactate, calcium chloride, sodium chloride, or the like. The electrically conducting high surface area particles 18 can be made with an extremely high level of porosity, thereby resulting in very high surface areas. For example, the electrically conducting high surface area particles 18 can each have a surface area of at least 1000 $m^2/g$. Each of the electrically conducting high surface area particles 18 can store a large amount of electrical charge. The electrical charge can be converted to an ionic charge and transmitted by the ionically conducting material. As an example, the electrically conducting high surface area particles 18 can include conductive carbon (e.g., Norit DLC SE30, Kuraray YP-50F, YP80F, and the like). In another example, the electrically conducting high surface area particles 18 can be platinum particles, iridium oxide particles, or any number of other electrically conductive high surface area particles. In some instances, the electrically conducting high surface area particles 18 can all be of the same material. In other instances, the electrically conducting high surface area particles 18 can be made of a variety of different materials. In some instances, an additive, such as a conductive carbon additive (e.g., Cabot XC-72, Timcal Super P carbons, carbon nanotubes, graphene, and the like), can be added to the slurry to improve the electrical conduction to the high surface area particles.

IV. Systems

Another aspect of the present disclosure can include a system 20 (FIG. 2) that can that can block conduction in neural tissue using at least one slurry electrode 10 (also referred to as a device 10) in FIG. 1. In addition to the device 10, the system can also include a direct current (DC) generator 22, which can generate a DC for application by the device 10. The device 10 can receive the DC in the slurry (e.g., via the connector 16), convert the DC to an ionic current, and transmit the ionic current through the ionically conductive membrane 14 to the nerve. The system 20 can also include additional components for generating and/or transmitting the DC to the device 10. For example, the system 20 can also include a return 24 device to return the current to the DC generator 22. In some instances, the return 24 can be remote. In other instances, the return 24 can be local to the DC generator 22.

The DC generator 22 can be configured or programmed to generate a DC of sufficient amplitude to cause the nerve conduction block. In some instances, the DC used for nerve conduction block can require a current with a large amplitude to be delivered to the nerve. For example, the current required may be 2 mA for 10 seconds, requiring a total electrical charge to be transferred of approximately 20 mC or more. Accordingly, the DC generator 22 can be any device configured or programmed to generate the specified current for application to a nerve to achieve an alternation in conduction thereof. One example of a DC generator 22 is a battery-powered, portable generator. Another example of a DC generator 22 is an implantable generator (IPG). It will be appreciated that the DC generator 22 can include additional components to selectively configure the current waveform, such as an amplitude modulator (not shown). In some instances, the generated DC can have an anodic polarity or a cathodic polarity, and an amplitude sufficient to cause the nerve conduction block. The DC generator 22 can be configured or programmed to generate a DC having monophasic waveform or a biphasic waveform, with one phase cathodic and one anodic.

The DC generator 22 can be coupled to the connector 16 of the device 10 to deliver the DC to the slurry. Within the slurry, the DC can be stored by the electrically conducting high surface area particles 18 and converted to an ionic current transmitted within the ionically conducting material 17. The ionic current can be transmitted through the ionically conductive membrane 14 to the neural tissue.

Figure 4:
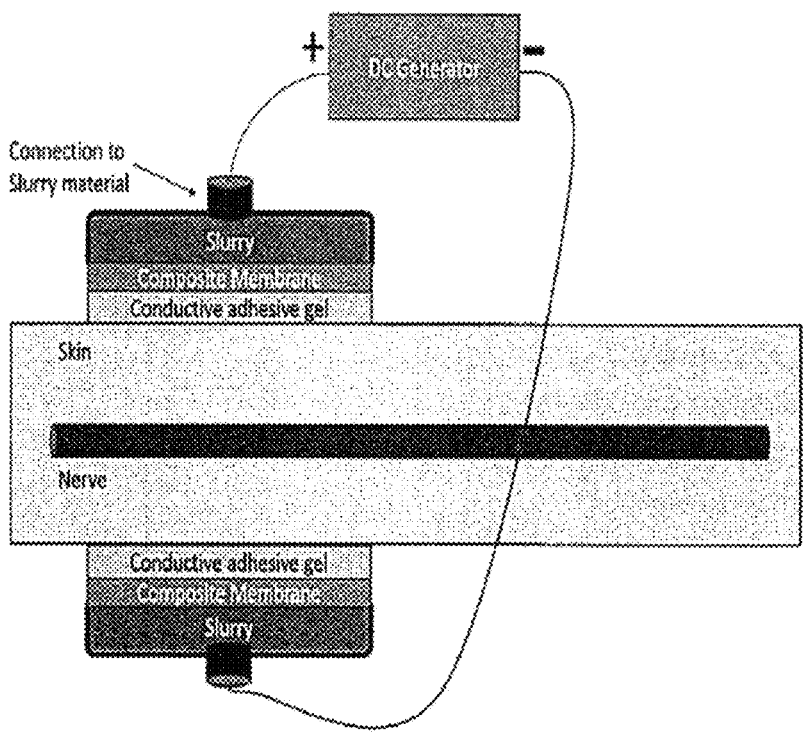

The device 10 can be configured as a surface/transcutaneous electrode (shown in FIGS. 3-4—including a conductive adhesive gel), a percutaneous electrode (shown in FIG. 5), or a subcutaneous (cuff) electrode (shown in FIG. 6). In any of these examples, the device 10 can use the slurry to provide a small form factor high capacitance electrode. The membrane prevents the migration of slurry material to the nerve surface, preventing the possibility of a reaction from the slurry material, while allowing ionic current to flow. A wire connecting to a DC generator can be inserted all the way to the tip of the electrode (without contacting the membrane), reducing the impedance of the electrode. The volume of the slurry available for charge transfer can include an entire length of a tubing housing mechanism, thereby increasing the capacitance. An example of such a percutaneous electrode can include a 4 mm diameter tube with 3 g of YP 50F carbon dispersed in 7 g of 1 wt % NaCl solution as the slurry material. A composite membrane of non-porous poly (vinyl alcohol) was deposited on a substrate of Daramic 175. A platinum wire connector was used. For the surface electrode example, a wicking material was used to fill the skin side of the membrane holder (a biocompatible gel could also be used in place of or in addition to the wicking material).

V. Methods

Figure 7:
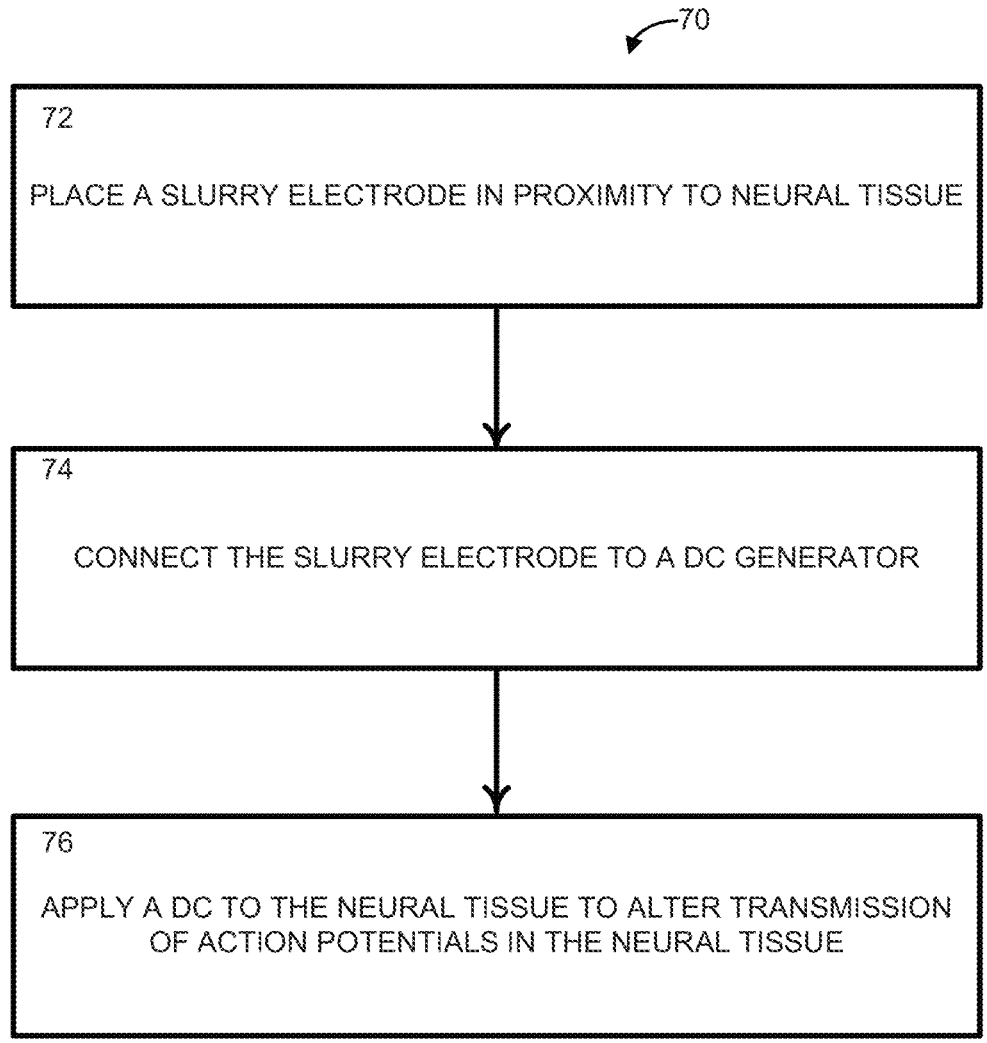
FIG. 7 is a process flow diagram illustrating a method for establishing DC nerve conduction block in neural tissue according to another aspect of the present disclosure.

Another aspect of the present disclosure can include a method 70 (FIG. 7) for establishing a direct current (DC) nerve conduction block in neural tissue. The method 70 can be executed using the system 20 shown in FIG. 2 using the slurry electrode 10 of FIG. 1 and described above. Advantageously, the slurry electrode 10 can be capable of delivering the charge required for nerve conduction block applications, while avoiding the generation of damage-causing non-reversible reaction products and exhibiting robust mechanical properties so that the charge can be predictably delivered. In other words, the method 70 can deliver the DC nerve conduction block safely without generating irreversible reaction products, thereby increasing patient safety and increasing the potential for clinical adoption.

The method 70 can include the steps of: placing a slurry electrode in proximity to neural tissue (Step 72); connecting the slurry electrode to a DC generator (Step 74); and applying a DC to the neural tissue to alter transmission of action potentials in the neural tissue (Step 76). The method 70 is illustrated as process flow diagrams with flowchart illustrations. For purposes of simplicity, the method 70 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 70.

At Step 72, a slurry electrode (e.g., element 10 of FIGS. 1 and 2) can be placed in proximity to neural tissue. In some examples, the neural tissue can include a peripheral nerve (e.g., motor, sensory, enteric and/or autonomic) or a nerve or nervous tissue comprising the central nervous system (e.g., brain and/or spinal cord). The slurry electrode can be placed, for example, on the surface of a patient's skin, percutaneously through the patient's skin, and/or subcutaneously (e.g., beside or around at least a portion of the nerve like a cuff). The slurry electrode (as shown in FIG. 1) can be made an ionically conductive membrane (e.g., element 14 of FIG. 1) having a first side and a second side and a mechanism (e.g., element 12 of FIG. 1) that is configured to encapsulate a slurry against the first side of the ionically conductive membrane. The slurry can include an ionically conductive material (e.g., element 17 of FIG. 1) and a plurality of electrically conducting high surface area particles (e.g., element 18 of FIG. 1). The mechanism and the first side of the ionically conductive membrane make up a housing for the slurry.

Figure 2:
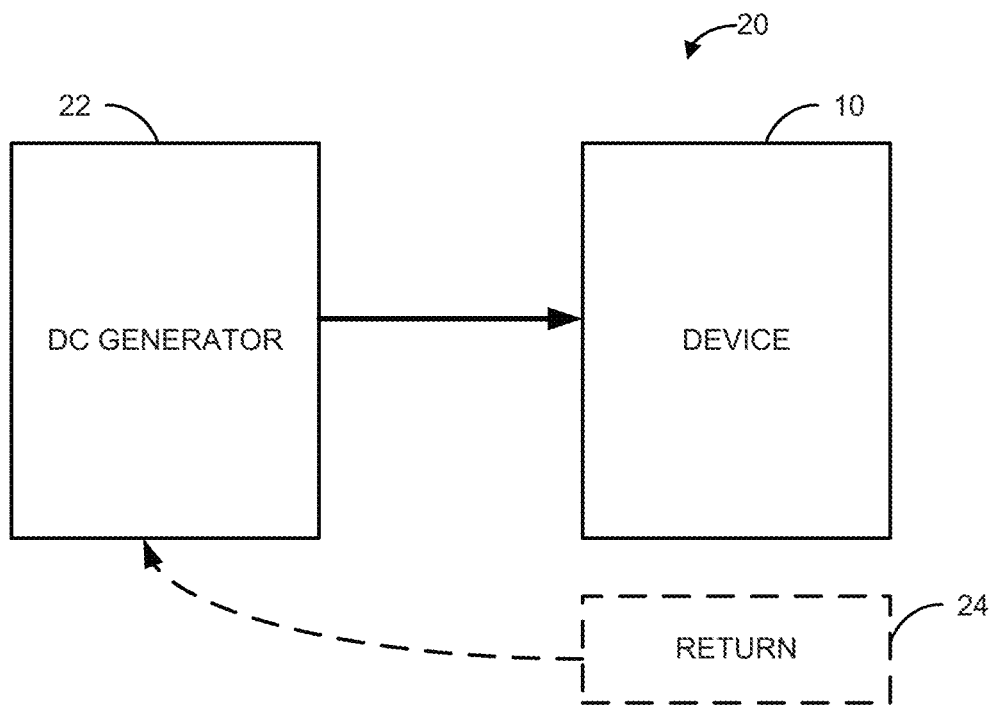
FIG. 2 is a schematic diagram of a system that can block conduction in neural tissue using the slurry electrode in FIG. 1.

At Step 74, the slurry electrode can be connected to a DC generator (e.g., element 22 of FIG. 2). The connection can be established by a connector (e.g., element 16 of FIG. 2) and one or more wires between the DC generator and the slurry electrode. The connector can contact a portion of the slurry without contacting the ionically conductive membrane, creating a connection between the slurry and the DC generator.

At Step 76, a DC (generated by the DC generator 22) can be applied to the neural tissue (by the slurry electrode 10) to alter transmission of action potentials in the neural tissue. The DC can be anodic and/or cathodic (monophasic or biphasic) and can have an amplitude sufficient to alter transmission of action potentials in the neural tissue. The transmission of the action potentials in the neural tissue can be altered based on the applied DC without causing damage to the neural tissue and/or device as a result of reaction products. The absence of damaging reaction products being delivered to the neural tissue is because, within the slurry, the DC electrical signal can be converted to an ionic signal, which is delivered to the neural tissue.

VI. Examples

Direct current (DC) nerve conduction block is fast acting, reversible, onset free, and easy to modulate, making it ideal for a variety of applications in a patient's nervous system. The slurry electrode shows immense opportunities for expanding DC nerve conduction block solutions to neurological diseases. It will be appreciated that the DC nerve conduction block can be applied to one or more neural structures related to the central nervous system, peripheral nervous system, autonomic nervous system, and enteric nervous system. However, described below are certain examples of some of the various medical conditions for which DC nerve conduction block can be used. The following examples are for the purpose of illustration only is not intended to limit the scope of the appended claims.

Motor System

In the motor system, spasticity is a debilitating condition that is a result of many different neurological conditions. A few examples of such neurological conditions include cerebral palsy, multiple sclerosis, spinal cord injury and stroke. In each example, the onset of spasticity results in many impairments and limitations including, but not limited to, gait disorders, fatigue, restricted range of movement, abnormal limb postures, quality of life issues, problems with activities of daily living, and/or pain, all of which impact the patient's quality of life. In addition to the quality of life impact of spasticity, the economic burden of any neurological condition increases significantly at the onset of spasticity. For stroke, it has been demonstrated that spasticity causes a four-fold increase in the direct costs associated with treating stroke patients. DC nerve conduction block applied by a slurry electrode can provide a solution that can minimize spasticity while maintaining muscle tone allowing for previously unattainable functional improvements.

Sensory System

In the sensory system, chronic neuropathic pain would be an ideal target for DC nerve conduction block applied by a slurry electrode. Neuropathic pain follows trauma or disease affecting the peripheral or central nervous system. Examples of such trauma can include physical trauma, spinal cord injury, while examples of such disease can be a side effect of chemotherapy, radiation, or surgery.

With some peripheral neuropathic pain, the source of the pain is localized at a neuroma. As is common with amputations, when a peripheral nerve is damaged, the peripheral nerve tries to regenerate itself towards the distal target. If the distal target is unavailable, axon sprouts grow into the surrounding scar tissue forming a neuroma, which can cause chronic pain and hypersensitivity. A neuroma is particularly well suited to DC nerve conduction block given the local nature of the condition. Also, the slurry electrode used for the DC nerve conduction block can easily be removed and placed in a different location, making the DC nerve conduction block desirable in the event that the neuroma changes in a way that lessens the effect of the nerve block.

Autonomic System

In the autonomic system, the properties of DC nerve conduction block provide a unique opportunity for modulation of neural activity. The autonomic nervous system frequently operates around a baseline of neural activity, which is modulated up or down to produce the desired physiological effects. For example, blood pressure is maintained through tonic activity in the autonomic nervous system. It would be extremely beneficial to not only be able to enhance neural activity, but also to inhibit neural activity in a graded/modulated manner Direct current can be modulated to affect a sub-population of axons to achieve a graded response. In the autonomic system, the onset response is particularly confounding since the effect is prolonged due to the dynamics of the system. The ability to produce an onset free nerve conduction block is absolutely critical to provide an effect solution to autonomic diseases.

The slurry electrode can be used to provide onset free DC nerve conduction block to the autonomic system. For example, the slurry electrode can be configured to apply the DC nerve conduction block in a subcutaneous manner Additionally, the DC can be modulated to affect a sub-population of axons to achieve a graded response.

Regional Applications

Some regional applications are well suited to DC nerve conduction block intervention. As an example, damage to the occipital nerve can result in chronic headache symptoms. Pharmacological nerve blocks, which are often used to treat this condition, could easily be replaced with a minimally invasive DC nerve conduction block applied by a slurry electrode, which would provide a longer term relief. As another example, the pudendal nerve has successfully been blocked using KHFAC and nerve cuff electrodes for bladder control, but the DC nerve conduction block applied by a slurry electrode would remove the onset response of the KHFAC block. Also, the DC would be capable of providing smooth transitions between partial and complete block which could further improve the functionality of the application.

From the above description, those skilled in the art will perceive improvements, changes and modifications. Such improvements, changes and modifications are within the skill of one in the art and are intended to be covered by the appended claims.

The following is claimed:

1. A method comprising:
   placing a slurry electrode in proximity to neural tissue;
   connecting the slurry electrode to a DC generator; and
   applying a DC waveform generated by the DC generator to the neural tissue via the slurry electrode,
   wherein the slurry electrode comprises a slurry of a plurality of electrically conducting high surface area particles each suspended in an ionically-conductive material and an ionically conductive membrane to prevent the slurry from contacting the neural tissue, wherein the slurry converts an electrical charge of the DC waveform to an ionic charge, and wherein the ionic charge is transmitted to the neural tissue through the ionically conductive membrane.

2. The method of claim 1, wherein the neural tissue comprises a peripheral nerve or a portion of a central nervous system.

3. The method of claim 1, wherein the slurry electrode is placed on a surface of a patient's skin in proximity to the neural tissue.

4. The method of claim 1, wherein the slurry electrode is placed percutaneously through the patient's skin in proximity to the neural tissue.

5. The method of claim 1, wherein the slurry electrode is placed subcutaneously beside or around at least a portion of the neural tissue.

6. The method of claim 1, wherein the slurry is encapsulated within a housing by the ionically conductive membrane.

7. The method of claim 1, wherein the DC generator is connected to the slurry electrode such that it does not contact the ionically conductive membrane.

8. The method of claim 1, wherein the DC waveform is configured to alter transmission of action potentials in the neural tissue without causing damage to the neural tissue and/or the slurry electrode.

9. The method of claim 1, wherein the DC waveform is configured to cause DC nerve conduction block.

10. A system comprising:
    at least one slurry electrode comprising an ionically conductive membrane and a slurry of a plurality of electrically conducting high surface area particles each suspended in an ionically-conductive material, wherein the ionically conductive membrane is configured to hold the slurry;
    a current generator coupled to the at least one slurry electrode configured to deliver direct current (DC) waveform for stimulation of neural tissue,
    wherein the slurry is configured to convert an electrical charge of the DC waveform to an ionic charge that is transmitted to the neural tissue, and wherein the ionically conductive membrane is configured to transmit only the ionic charge to the neural tissue.

11. The system of claim 10, wherein the slurry is encapsulated within a housing by the ionically conductive membrane configured for ionic conduction.

12. The system of claim 10, wherein the ionically conductive membrane is configured to allow ionic charge to flow therethrough.

13. The system of claim 10, wherein the ionically conductive membrane has a first side and a second side with the first side comprising a porous substrate material and the second side comprising a non-porous film.

14. The system of claim 13, wherein the ionically conductive membrane comprises a composite material of the non-porous film deposited on the porous substrate material.

15. The system of claim 10, wherein the ionically conductive material prevents the slurry from contacting neural tissue.

16. The system of claim 10, further comprising a connector configured to establish an electrical connection between the slurry of the at least one slurry electrode and the DC generator.

17. The system of claim 16, wherein the connector comprises at least one of a wire, a foil, a mesh.

18. The system of claim 17, wherein the connector further comprises at least a portion of a housing mechanism configured to house the slurry.

19. The system of claim 10, wherein each of the plurality of electrically conducting high surface area particles comprise surface areas of at least 1000 $m^2/g$.

20. The system of claim 10, further comprising a return device configured to return the DC waveform to the generator.

\* \* \* \* \*